United States Patent [19]

Magistro

[11] Patent Number: 5,008,225
[45] Date of Patent: Apr. 16, 1991

[54] CATALYTIC DEHYDROHALOGENATION CATALYST

[75] Inventor: Angelo J. Magistro, Brecksville, Ohio

[73] Assignee: The B. F. Goodrich Company, Akron, Ohio

[21] Appl. No.: 372,589

[22] Filed: Jun. 27, 1989

Related U.S. Application Data

[60] Continuation-in-part of Ser. No. 72,324, Jul. 13, 1987, abandoned, Division of Ser. No. 613,551, May 24, 1984, abandoned.

[51] Int. Cl.$^5$ .................. B01J 27/10; B01J 29/06
[52] U.S. Cl. ............................. 502/73; 502/65
[58] Field of Search ..................... 502/65, 73, 60

[56] References Cited

U.S. PATENT DOCUMENTS

| | | | |
|---|---|---|---|
| 2,765,351 | 10/1956 | Conrad | 260/656 |
| 2,838,577 | 6/1958 | Cook et al. | 260/656 |
| 2,877,277 | 3/1959 | Gattiker et al. | 260/656 |
| 3,290,399 | 12/1966 | Braconier et al. | 260/656 |
| 3,395,096 | 7/1968 | Gladrow | 208/111 |
| 3,547,831 | 12/1970 | Oleck et al. | 252/455 |
| 3,558,735 | 1/1971 | Beard, Jr. | 502/224 |
| 3,637,872 | 1/1972 | Berkowitz | 260/654 D |
| 3,679,604 | 7/1972 | Lee et al. | 252/455 Z |
| 3,896,182 | 7/1975 | Young | 260/656 R |
| 3,927,131 | 12/1975 | Ward | 260/654 D |
| 3,930,987 | 1/1976 | Grand | 208/111 |
| 3,957,623 | 5/1976 | McDaniel et al. | 208/120 |
| 4,312,744 | 1/1982 | Tu et al. | 502/65 |
| 4,384,159 | 5/1983 | Diesen | 208/111 |

FOREIGN PATENT DOCUMENTS

| | | |
|---|---|---|
| 0010362 | 4/1980 | European Pat. Off. . |
| 2487064 | 11/1964 | Japan . |
| 5073501 | 1/1972 | U.S.S.R. . |
| 3616291 | 1/1979 | U.S.S.R. . |

OTHER PUBLICATIONS

A. Maccoll, Heterolysis and the Pyrolysis of Alkyl Halides in the Gas Phase, Chemical Review 1968, p. 42–44.

P. Ashmore, Chlorine-Catalyzed Pyrolysis of 1-2-Dichloroethane, J. Am. Chem. Soc. Fareday Transactions 1, 1982, 78, pp. 677–6.

Soviet Inventions Illustrated, Abstract No. A41E16, Aug. 26, 1981, Derwent Pub. Ltd.

Soviet Inventions Illustrated, Abstract No. J04E16, Apr. 13, 1983, Derwent Pub. Ltd.

*Primary Examiner*—Carl F. Dees
*Attorney, Agent, or Firm*—Thoburn T. Dunlap

[57] ABSTRACT

The invention is an improved catalyst and process for the manufacture of vinyl chloride from ethylene dichloride. Specifically, the invention is an improved catalyst for the catalyzed dehydrohalogenation of ethylene dichloride in the presence of oxygen. The catalyst comprises a rare earth metal chloride on a zeolite. The catalyst and process enables one to conduct the dehydrohalogenation (or cracking) operation at significantly lower temperatures than employed using a thermal process, without the coking problems observed in such cracking processes.

8 Claims, No Drawings

CATALYTIC DEHYDROHALOGENATION CATALYST

This is a continuation-in-part of copending application Ser. No. 07/072,324 filed on July 13, 1987 which is a Divisional of application Ser. No. 06/613,551 filed on May 24, 1984 (both abandoned).

BACKGROUND OF THE INVENTION

It is well known that vinyl chloride monomer (VCM) can be produced from 1,2-dichloroethane (commercially called ethylene dichloride or EDC) by splitting off a molecule of hydrogen chloride. The dehydrohalogenation reaction (commonly called "cracking" in the trade) is typically accomplished by heating the EDC, in the absence of a catalyst, in an inert atmosphere using high temperature and pressure; usually about 550° C. and at a pressure of about 300 to 600 psi (21-42 Kilograms/centimeter$^2$; 2,070,000 to 4,140,000 Pascals).

A serious disadvantage of the standard Pyrolysis or thermal process is the need of a large amount of costly heat energy to accomplish the cracking. Another serious difficulty encountered in such a process is the rapid deposition of solid by-products (coke) on the tubes which limits the process to relatively short operating periods before cleaning of the tubes is required. Lastly, in these high temperature processes, undesirable side reactions frequently occur which lower the conversion of EDC.

To reduce the problems observed in the standard pyrolytic cracking process various catalytic processes have been proposed. For example, U.S. Pat. No. 2,877,277 teaches the use of an alkaline earth metal hydroxide in aqueous solution to promote the dehydrochlorination of EDC to VCM, and refers to the prior use of alkali metal hydroxides. These processes suffer from the disadvantages of a very long contact time (30 minutes to 2.5 hours) and difficulty in the separation and purification of the resultant VCM from the aqueous solution.

U.S. Pat. No. 3,290,399 teaches the use of graphite to promote the cracking reaction, and references the use of activated carbon washed with nitric acid as disclosed in British Patent No. 823,285. The processes suffer in that reaction temperatures and pressures are still high, up to 600° C.

Japanese Patent No. 24870/64 teaches the use of a catalyst of a boron compound such as boric acid on activated charcoal.

Lastly, U.S. Pat. No. 3,896,182 teaches that the clogging of Pyrolysis reactor tubes by carbonaceous substances (coking) can be reduced by conducting the reaction in the substantial absence of oxygen, below 2.0 ppm of oxygen present.

While such processes may be commercially feasible, there has been and still is a continuing search for catalytic materials which will improve the dehydrohalogenation process by enabling the use of lower operating temperatures and pressures and further reduction in undesirable side reactions and coking.

SUMMARY OF THE INVENTION

It has been unexpectedly found that conversion of EDC to VCM with less energy expenditure and reduced coking can be obtained by a process which comprises dehydrohalogenating the EDC to VCM, in the presence of oxygen, employing, as a catalyst, a composition comprising a rare earth metal chloride on a zeolite. Using the rare earth metal chloride-zeolite catalysts of the instant invention, the cracking Process can be operated at a temperature as low as 150° C. up to 500° C., and more preferably from about 200° C. to about 350° C., at pressures from atmospheric to about 300 psi (1-21 Kilograms/centimeter$^2$; 101,400-2,070,000 Pascals).

DETAILED DESCRIPTION

Vinyl chloride monomer (VCM) can be prepared by various processes, but the most common process involves the formation of EDC by the reaction between ethylene and chlorine or hydrogen chloride, followed by a dehydrohalogenation step wherein the EDC is thermally cracked under pressure to VCM and by-product hydrogen chloride. The hydrogen chloride is typically recovered and used in an oxyhydrochlorination step wherein the hydrogen chloride is reacted with additional ethylene to produce EDC which is, in turn, fed to the cracking step. The VCM is recovered, purified, and used extensively as a monomer in the manufacture of polyvinYl chloride (PVC) resins, a large volume, versatile plastic material.

In the typical cracking process, large amounts of natural gas are burned to supply the heat energy to operate the cracking furnaces. In these processes, the EDC is vaporized and passed through a tube-type furnace which is directly heated to a temperature in the range of about 500° C. to about 600° C. In the Present, standard commercial cracking process no solid cracking catalyst is employed. In the absence of a catalyst, the reaction is a thermally induced dehydrochlorination whereby one molecule of hydrogen chloride is split out of each EDC molecule, resulting in one molecule of VCM.

The present invention encompasses the use of many process design configurations such as a single fluid-bed with reactants fed into the reaction zone through a distributor plate, fluid cat cracking technology where the oxygen is fed in at a separate regeneration zone in the reactor, a fixed bed cracking furnace, or any other known designs. The heat energy can be supplied in any known manner, but typically is supplied by burning natural gas. The EDC is vaporized and passed through the fluid bed or tubes in the furnace where the catalyst is present. The ratio of oxygen to EDC in the feed stream is controlled to accomplish the objectives of this invention and yet operate safely.

The temperatures employed in the present Process range from as low as 150° C. up to about 500° C., more Preferably from about 200° C. to about 350° C., and most preferably from about 250° C. to about 325° C. In the process, pressures will range from about one atmosphere (1 kilograms/centimenter$^2$; 101,400 pascals) up to twenty (20) (21 kilograms/centimeter$^2$; 2,070,000 pascal) or more atmospheres, but more typically range from about five (5) to about fifteen (15) atmospheres (5-11 kilograms/centimeter$^2$; 507,000-1,520,000 pascals).

A critical feature of the present invention comprises the use of an improved catalyst for the cracking step. Specifically, the catalyst is comprised of a rare earth metal chloride deposited on a zeolite supPort. Both natural and synthetic zeolites can be used in the present invention. Examples of natural zeolites are analcite, erionite, chabazite, faujasite, mordenite, gmelinite, mazzite, offertite, heulandite, natrolite, stilbite, and thomsonite.

The synthetic zeolites can be made in a variety of forms ranging from gelatinous to porous and sandlike. Examples of known synthetic zeolites are Type A (described in U.S. Pat. No. 2,882,243); Type X (described in U.S. Pat. No. 2,882,244); Type Y (described in U.S. Pat. No. 3,130,007); Type R (described in U.S. Pat. No. 3,030,181); and other zeolites as described in the Dec. 13, 1982 article in "Chemical and Engineering News" entitled "Shape Selectivity Key to Designed Catalysts" by Mr. Joseph Hoggin. For the purposes of this invention, the solid zeolites are Preferred, and particularly those synthetic solid zeolites having pore openings of 5A or more. Synthetic zeolites having a pore opening of over 5A are readily available commercially from Englehard Minerals and Chemicals and Linde Division of Union Carbide Corporation. Examples of such commercially-available zeolites are Englehard's HFZ-20, HFZ-33, and HEZ-55.

The rare earth metal chloride(s) of the present invention must be combined with a zeolite. The combination of rare earth metal chloride(s) and a zeolite, when utilized in the presence of oxygen, permits the conversion of EDC to VCM with less energy expenditure and allows for a selective catayst that maintains activity with time. Other support materials (e.g., alumina, alumino-silicates, and the like) when utilized under similar conditions exhibit lower conversions and selectivities.

The rare earth metal chloride can be the chloride of any rare earth metal as found in the Periodic Table numbers 57 (lathanum) through 71 (lutetium). The rare earth metals lathanum (La), praeseodymium (Pr), neodymium (Nd), and the rare earth metal mixture dydinium which consists essentially of La, Nd, Pr, samarium (Sm) and cerium (Ce), are all readily available and, hence, are preferred rare earth metals. The most preferred rare earth metal is lanthanum, and the most preferred rare earth metal chloride is lathanum chloride ($LaCl_3$).

The amount of rare earth metal chloride employed with the zeolite can be from about 0.1% upto 30% by weight of the total weight of the catalyst. Preferably, the weight of the rare earth metal chloride is from about 2% to about 20% by weight, more Preferably from about 4% to about 16% by weight, and most preferably 8% by weight. Of course, the optimum level of rare earth metal chloride on the zeolite may vary with the type of zeolite employed. The catalysts of this invention can optionally contain levels of other metals which are often used to impart stability and the like. Examples of such optional materials are alkali and alkaline earth metal oxides and chlorides such as lithium and potassium oxide and chloride, magnesium chloride, and strontium chloride. These additional metals can be employed in up to 5% by weight based on the total weight of the catalyst.

The rare earth metal chloride(s), and other optional metal chlorides and oxides, can be deposited on the zeolite in any known manner. Preferably, an aqueous solution(s) of the metal(s) is prepared and contacted with the zeolite, which mixture is then filtered and dried at temperatures below about 200° C., followed by calcination at a temperature from about 300° C. to about 500° C. for about 2 to 16 hours. A calcination temperature of about 500° C. is most preferred. Calcining the catalYst mixture at higher temperatures, especially above 560° C., reduces the stability and/or effectiveness of the resultant catalyst due to the conversion of the rare earth metal chloride to the rare earth metal oxide. Calcination temperatures above 500° C. may be utilized so long as an effective amount of the rare earth metal chloride is present on the finished catalyst. It will be recognized, however, that the amount of rare earth chloride that is converted to the rare earth oxide at the higher temperatures is, of course, dependent upon the temperature employed and duration of the calcination procedure. The concentration of the metal(s) in the aqueous solution(s) is determined by the desired level of metal on the final catalyst. If more than one metal is added to the zeolite, this can be done simultaneously or sequentially by adding each metal after each drying step. It is possible to add part or all of the metal(s) to the zeolite while the zeolite is in the reactor area, and also to add additional metal(s) to the zeolite during operation to replenish metal(s) lost during the reaction.

The zeolite chosen should have a form or particle size permitting it to be conveniently placed or packed in the cracking reactor. The rare earth metal chloride-zeolite catalyst is placed in the cracking reactor in such fashion as to allow the passage of vapor therethrough. The catalyst may be fixed in the reactor bed or used as a fluidized bed. Typically, the cracking reactor is purged with nitrogen before the EDC and oxygen are introduced into the reactor. When the EDC comes in contact with the catalyst the dehydrochlorination reaction or cracking proceeds smoothly, rapidly converting the EDC to VCM and by-product HCl.

The amount of oxygen employed in the process, either as pure oxygen or air, is from about 0.05 mole to about 0.5 mole of oxygen per mole of EDC. Below 0.05 mole, increased carbon buildup is observed, and above 0.5 mole, increased formation of carbon oxides is observed. The preferred molar ratio of oxygen to EDC employed is from about 0.15 mole to 0.3 mole per mole of EDC. Not all the oxygen need be added in the reaction zone; i.e. the oxygen can be staged or added in a separate zone. The oxygen is added to the reactor in a manner and flow to ensure safety and operations under non-explosive conditions.

While the cracking reaction may be operated at atmospheric Pressure, it is preferred in the present invention to operate at superatmospheric pressures of from about 5 to 20 atmospheres (5-11 kilograms/centimeter$^2$; 507,000-1,520,000 pascals). Generally, at higher pressures, less coking and less formation of undesirable chlorohydroCarbon by-products, such as $CCl_4$, occurs than when operating at atmospheric pressure. If necessary, the reactor can be shut down and the carbon formation, if any, can be readily removed by conventional means; i.e. heating the reactor at elevated temperatures usually in the range of over 300° C. to about 700° C. Also, the carbon can be removed and the catalyst regenerated in a continuous manner using a fluid cat cracking reactor design as shown in the "Chemical and Engineering News" article previously referenced.

The reaction or contact time of the EDC with the catalyst in the reactor can be varied depending on the volume and shape of the reactor and the flow rate of EDC and oxygen. The contact time necessary between the EDC and catalyst to Promote the desired dehydrochlorination reaction is obtained by controlling the space velocity of the gaseous material passing through the reaction zone. It has been found, however, that for most reactors a contact time as high as about 60 seconds and as low as 0.5 second can be employed. If the contact time is too low the quantity of unreacted EDC is too high. On the other hand, if the contact time is too high, the amount of carbon oxide and by-product impurities increase. One can readily adjust the gaseous feed rate to obtain the optimum contact time for any particular type reactor. Contact times in the experiments detailed in the following Examples ranged from about 5 seconds to about 30 seconds.

The gaseous mixture withdrawn from the reaction zone can be passed directly to a condenser to recover the condensable materials including the EDC, and hydrogen chloride Passed overhead to be collected, and then often recycled to an oxyhydrochlorination process to be used in making more EDC. Alternatively, the gases leaving the reaction zone can be cooled and subjected to fractional distillation under pressure, preferably at lower pressure than that used for the cracking. The hydrogen chloride separates first and is recovered or recycled. The uncondensed gases can be vented into a separate recovery or treatment zone wherein the VCM and unreacted EDC are recovered and fractionally distilled to remove the VCM. The unreacted EDC is recycled to the cracking zone.

Present commercial cracking processes typically operate at above 500° C. to 600° C., at pressures of 300 to 600 Psi (21–42 kilograms/centimeter$^2$; 2,070,000–4,140,000 pascals), and have contact times of about 1 to 5 seconds. For example, operating with no catalyst (thermal cracking only), at a temperature of 560° C. with a one second contact time, an EDC conversion of up to 80% can be obtained. At 530° C., the EDC conversion drops to about 50%, and at 500° C., the EDC conversion drops to about 20%. Operation below 500° C. is not economically feasible. Hence, the standard thermal EDC cracking processes require high temperature operation and very high energy use. Further, these processes typically suffer from high coking which necessitates shut down and decoking about once each month.

In contrast, the catalyst and process of this invention results in effective cracking of EDC to VCM with significant energy savings and little coke formation, thereby permitting long operation between shut downs. The formation of carbon oxides and by-product chlorinated hydrocarbon can be as low as under 10%. A Small amount, up to 5% and usually no more than 2%, of ethylene may be produced.

The following Examples are given to more specifically define the present invention. It is understood that the Examples are demonstrative and illustrative only, and not intended to be limiting of the invention. In the examples, all parts and percents are by weight, unless otherwise indicated.

Example of Preparation of Catalyst 500 grams of HEZ-55, a synthetic zeolite obtained from Englehard Minerals and Chemicals, was added to an aqueous solution of 5.77 grams of lanthanum chloride, (LaCl$_3$.6H$_2$O) in 40 cc of distilled water, and stirred to obtain uniform mixing. The mixture of LaCl$_3$ on HEZ-55 was filtered out of solution, dried at 110° C. for 16 hours, followed by calcination at 500° C. for 16 hours. The rare earth metal chloride-zeolite catalyst contained eight percent (8%) by weight of La metal as analyzed by X-Ray flourence.

The procedure was essentially repeated using HFZ-20 zeolite and HFZ-33 zeolite in Place of HEZ-55 zeolite, and varying the amount of LaCl$_3$ impregnated onto the zeolites. If and when additional, optional metals were added, such as lithium, potassium, magnesium, or strontium, these metals were also added as metal chloride salts in aqueous solution and were added simultaneously with the LaCl$_3$. Conditions of drying and calcination were essentially the same in all catalyst preparations, except as expresslY stated below.

Examples of the catalysts of the invention, prepared as described above, are: 8% LaCl$_3$ on HFZ-33; 8% LaCl$_3$, 4% LiCl on HFZ-33; 16% LaCl$_3$ on HFZ-33; 16% LaCl$_3$ on HFZ-55; 8% LaCl$_3$, 4% KCl on HFZ-55; 8% LaCl$_3$, 4% MgCl$_2$ on HFZ-20; and 8% LaCl$_3$, 4% SrCl$_2$ on HFZ-20.

Experiments

A series of experiments were conducted using a laboratory reactor comprising a 30 mm diameter by 45 cm. long glass reactor made of pyrex. The catalyst was placed in the reactor and the process was conducted as a one-pass, continuous fluid bed catalytic process. The reactor was first purged with nitrogen gas, followed by introduction of EDC and oxygen (as air). The exit gases were collected and periodic samples were analyzed for EDC, VCM, HCl and other products using a gas chromotograph, Model No. 810 made by Hewlett-Packard and using DC-200 as a packing material. The following examples show data that was obtained using the above-described apparatus and at the oxygen/EDC molar ratios, temperatures, and contact times as indicated, operating at a pressure of about 30 psi (2 kilograms/centimeter$^2$; 1,000,000 Pascals). Mol% Conversion of EDC was determined using the formula $$1 - \frac{\text{milimoles EDC out} \times 100}{\text{millimoles EDC feed in}}$$

and % yield of VCM, carbon oxides, and other products were determined as using the formula $$\frac{\text{milimoles product out} \times 100}{\text{EDC conversion}}$$

EXAMPLE 1

This example compares a rare earth metal chloride catalyst of the present invention to a rare earth metal oxide catalyst. The rare earth chloride (LaCl$_3$) catalysts were prepared as set forth in the example of preparation of catalyst and contained 8% LaCl$_3$. The rare earth oxide La$_2$O$_3$ were prepared as follows:

To 50 grams of HEZ-55 zeolite (Englehard Minerals and Chemicals) was added an aqueous solution of 9.09 grams of lanthanum nitrate (La(NO$_3$)$_3$.6H$_2$O) in 20 cc of distilled water. The ingredients were stirred to obtain uniform mixing. The mixture of La(NO$_3$)$_3$ on HEZ-55 was filtered out of solution and dried at 110° C. for 8 hours, followed by calcination at 560° C. for another 8 hours. There was obtained a lanthanum oxide/zeolite catalyst containing 8% La$_2$O$_3$ on HEZ-55.

The finished catalysts were tested as set forth in the previous examples. The data shows that the use of chloride salts of rare earth metals gives high yields of VCM without excess carbon oxides. In sharp contrast, the use of rare earth oxides gives low yelds of VCM and relatively high carbon oxide formation.

| Catalyst | $O_2$/EDC Ratio | Contact Time (Sec) | Temperature (°C.) | Mole % Conv. EDC | % Yield VCM | % Yield $CO + CO_2$ |
|---|---|---|---|---|---|---|
| $LaCl_3$ | 0.29 | 5.2 | 250 | 16.6 | 91.1 | 8.9 |
| $LaCl_3$ | 0.20 | 10.9 | 300 | 35.8 | 90.1 | 9.2 |
| $La_2O_3$ | 0.20 | 17.3 | 250 | 10.0 | 61.2 | 36.5 |
| $La_2O_3$ | 0.20 | 15.5 | 300 | 32.9 | 62.2 | 35.2 |

EXAMPLE 2

This example compares the use of zeolite alone (Z) as a catalyst versus the use of the following catalysts of the invention; (A) a catalyst of 8% $LaCl_3$ on zeolite (B) 8% $LaCl_3$, 4% LiCl on zeolite; and (C) 16% $LaCl_3$ on zeolite. The zeolite used was HFZ-33.

| Run | $O_2$/EDC Ratio | Contact Time (Sec) | Temperature (°C.) | Mole % Conv. EDC | % Yield VCM | % Yield $CO + CO_2$ |
|---|---|---|---|---|---|---|
| Z1 | 0.26 | 17.3 | 250 | 12.9 | 61.7 | 31.1 |
| 2 | 0.26 | 15.8 | 300 | 23.5 | 58.4 | 38.7 |
| 3 | 0.21 | 11.5 | 300 | 13.5 | 61.9 | 38.1 |
| A1 | 0.29 | 13.9 | 300 | 51.8 | 78.1 | 20.7 |
| 2 | 0.20 | 10.9 | 300 | 35.8 | 90.1 | 9.2 |
| 3 | 0.20 | 15.7 | 300 | 35.7 | 83.2 | 15.5 |
| B1 | 0.29 | 15.2 | 250 | 32.8 | 48.1 | 33.3 |
| 2 | 0.20 | 11.9 | 250 | 14.5 | 60.0 | 20.3 |
| 3 | 0.20 | 10.9 | 300 | 41.3 | 68.7 | 21.9 |
| C1 | 0.29 | 15.2 | 250 | 10.6 | 64.1 | 33.4 |
| 2 | 0.29 | 13.9 | 300 | 24.9 | 57.0 | 41.4 |
| 3 | 0.20 | 10.9 | 300 | 12.5 | 59.9 | 38.2 |

As can be seen from the data, the use of a catalyst of a rare earth metal chloride on zeolite results in significantly higher EDC conversion. The level of 16% $LaCl_3$ has exceeded the optimum concentration on the HFZ-33 zeolite. Example 5 shows a level of 16% $LaCl_3$ on HFZ-55.

EXAMPLE 3

The following data is from runs using a catalyst of (A) 8% $LaCl_3$ on HFZ-33 and (B) 8% $LaCl_3$, 4% LiCl on HFZ-33.

| Run | $O_2$/EDC Ratio | Contact Time (Sec) | Temperature (°C.) | Mole % Conv. EDC | % Yield VCM | % Yield $CO + CO_2$ |
|---|---|---|---|---|---|---|
| A | | | | | | |
| 1 | 0.29 | 5.2 | 250 | 16.6 | 91.1 | 9.1 |
| 2 | 0.29 | 4.8 | 300 | 37.7 | 86.9 | 13.1 |
| 3 | 0.20 | 10.9 | 300 | 35.8 | 90.1 | 9.2 |
| 4 | 0.20 | 15.7 | 300 | 38.9 | 83.3 | 15.4 |
| B | | | | | | |
| 1 | 0.29 | 15.2 | 250 | 32.8 | 48.1 | 34.3 |
| 2 | 0.29 | 13.9 | 300 | 50.2 | 59.6 | 33.0 |
| 3 | 0.20 | 10.9 | 300 | 41.3 | 68.7 | 21.9 |
| 4 | 0.20 | 15.7 | 300 | 42.2 | 65.4 | 24.8 |

EXAMPLE 4

The example shows the use of catalysts of (A) 8% $LaCl_3$, 4% $MgCl_2$ on HFZ-20 and (B) 8% $LaCl_3$, 4% $SrCl_2$ on HFZ-20.

| Run | $O_2$/EDC Ratio | Contact Time (Sec) | Temperature (°C.) | Mole % Conv. EDC | % Yield VCM | % Yield $CO + CO_2$ |
|---|---|---|---|---|---|---|
| A | | | | | | |
| 1 | 0.29 | 15.2 | 250 | 28.8 | 46.8 | 41.6 |
| 2 | 0.20 | 5.8 | 300 | 12.0 | 60.4 | 30.3 |
| 3 | 0.20 | 10.9 | 300 | 25.4 | 69.0 | 29.9 |
| 4 | 0.20 | 26.1 | 300 | 63.9 | 60.0 | 30.4 |
| B | | | | | | |
| 1 | 0.29 | 15.2 | 250 | 35.1 | 36.7 | 57.7 |
| 2 | 0.20 | 17.2 | 250 | 11.7 | 65.0 | 30.7 |
| 3 | 0.29 | 13.9 | 300 | 31.3 | 52.5 | 44.6 |
| 4 | 0.20 | 15.7 | 300 | 25.3 | 54.1 | 42.6 |
| 5 | 0.20 | 10.9 | 300 | 20.5 | 63.4 | 33.2 |
| 6 | 0.20 | 6.9 | 300 | 17.7 | 73.0 | 26.0 |

EXAMPLE 5

This example shows the use of a catalyst of 8% $LaCl_3$ on HFZ-33 which was converted to the oxide by calcination at (a) 700° C. and (b) 900° C.

| Run | $O_2$/EDC Ratio | Contact Time (Sec) | Temperature (°C.) | Mole % Conv. EDC | % Yield VCM | % Yield $CO + CO_2$ |
|---|---|---|---|---|---|---|
| a | | | | | | |
| 1 | 0.29 | 15.2 | 250 | 29.9 | 56.5 | 39.8 |
| 2 | 0.29 | 13.9 | 300 | 42.5 | 63.8 | 33.3 |
| 3 | 0.20 | 17.2 | 250 | 13.8 | 80.5 | 19.3 |
| 4 | 0.20 | 15.7 | 300 | 36.3 | 71.9 | 26.4 |
| 5 | 0.20 | 26.1 | 300 | 45.6 | 62.1 | 27.4 |
| b | | | | | | |
| 1 | 0.29 | 15.2 | 250 | 2.7 | 56.6 | 40.9 |
| 2 | 0.29 | 13.9 | 300 | 11.5 | 50.6 | 45.2 |
| 3 | 0.20 | 17.2 | 250 | 4.7 | 62.2 | 26.6 |
| 4 | 0.20 | 15.7 | 300 | 8.1 | 48.2 | 46.1 |
| 5 | 0.20 | 26.1 | 300 | 20.3 | 52.7 | 44.1 |

The data shows that as the catalyst is calcined above 560° C. and conversion of the rare earth chloride to the rare earth oxide takes place, the effectiveness of the catalyst is reduced relative to the preferred 8% $LaCl_3$ catalysts of the present invention.

EXAMPLE 6

The following data is from runs using a catalyst of 16% $LaCl_3$ on HFZ-55.

| Run | $O_2$/EDC Ratio | Contact Time (Sec) | Temperature (°C.) | Mole % Conv. EDC | % Yield VCM | % Yield $CO + CO_2$ |
|---|---|---|---|---|---|---|
| 1 | 0.29 | 15.2 | 250 | 22.1 | 71.9 | 24.5 |
| 2 | 0.20 | 17.2 | 250 | 16.8 | 65.1 | 26.1 |
| 3 | 0.20 | 28.6 | 250 | 26.8 | 56.0 | 37.5 |
| 4 | 0.29 | 13.9 | 300 | 27.9 | 52.5 | 42.4 |
| 5 | 0.20 | 26.1 | 300 | 23.8 | 55.9 | 36.6 |
| 6 | 0.20 | 15.7 | 300 | 34.9 | 61.2 | 33.0 |
| 7 | 0.20 | 8.4 | 300 | 18.7 | 73.9 | 22.1 |
| 8 | 0.20 | 5.8 | 300 | 17.0 | 81.8 | 15.2 |

The data shows that higher conversions of EDC were obtained at 300° C. than 250° C. and that a contact time of about 15 seconds gave the best results.

I claim:

1. A dehydrohalogenation catalyst comprising from about 0.1% to about 30% by weight based on the total weight of the catalyst of at least one rare earth metal chloride deposited on a solid synthetic zeolite having a pore opening of at least 5A.

2. The catalyst of claim 1 wherein the rare earth metal is selected from the group consisting of lanthanum, proseodymiun, neodymium, and mixtures thereof.

3. The catalyst of claim 2 wherein the catalyst contains lanthanum chloride at from about 4 to about 16% by weight of the total weight of the catalyst.

4. The catalyst of claim 3 wherein the catalyst contains 8% lanthanum chloride by weight of the total weight of the catalyst.

5. The catalyst of claim 1 wherein the catalyst additionally contains about 5% by weight of an alkali and/or alkaline earth metal oxide or chloride.

6. A method of making a low temperature EDC cracking catalyst comprising:
    (a) depositing a rare earth metal chloride on a zeolite;
    (b) calcining the rare earth metal chloride deposited zeolite for a time and at a temperature wherein a substantial amount of the rare earth metal remains in the chloride form.

7. The method of claim 6 wherein said temperature is 500° C.

8. The method of claim 6 wherein the rare earth metal chloride deposited catalyst is dried before said calcination step.

* * * * *